(12) United States Patent
Tokuda et al.

(10) Patent No.: US 8,366,813 B2
(45) Date of Patent: Feb. 5, 2013

(54) PARTICULATE MATTER DETECTION DEVICE

(75) Inventors: Masahiro Tokuda, Nagoya (JP); Atsuo Kondo, Nagoya (JP); Takeshi Sakuma, Nagoya (JP); Takashi Egami, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 458 days.

(21) Appl. No.: 12/715,598

(22) Filed: Mar. 2, 2010

(65) Prior Publication Data

US 2010/0229724 A1 Sep. 16, 2010

(30) Foreign Application Priority Data

Mar. 12, 2009 (JP) ................................. 2009-058845

(51) Int. Cl.
*B03C 3/47* (2006.01)

(52) U.S. Cl. ... 96/19; 55/282.3; 55/DIG. 10; 73/864.71; 96/28; 96/69; 96/99

(58) Field of Classification Search .............. 96/18–24, 96/28, 69, 98, 99; 95/73; 55/282.3, DIG. 10; 73/28.02, 864.71
See application file for complete search history.

(56) References Cited

U.S. PATENT DOCUMENTS

| | | | | |
|---|---|---|---|---|
| 4,477,268 A | * | 10/1984 | Kalt | 96/99 |
| 4,944,778 A | * | 7/1990 | Yanagawa | 96/66 |
| 5,055,118 A | * | 10/1991 | Nagoshi et al. | 96/88 |
| 5,466,279 A | * | 11/1995 | Hattori et al. | 96/69 |
| 5,474,600 A | * | 12/1995 | Volodina et al. | 96/57 |
| 6,187,271 B1 | * | 2/2001 | Lee et al. | 422/121 |
| 7,077,890 B2 | * | 7/2006 | Botvinnik | 96/69 |
| 7,261,767 B2 | * | 8/2007 | Choi et al. | 96/69 |
| 7,294,176 B2 | * | 11/2007 | Kim et al. | 96/69 |
| 7,431,755 B2 | * | 10/2008 | Kobayashi et al. | 96/69 |
| 2004/0226448 A1 | * | 11/2004 | Griffiths et al. | 96/67 |
| 2006/0227486 A1 | * | 10/2006 | Kim et al. | 361/120 |

FOREIGN PATENT DOCUMENTS

| | | |
|---|---|---|
| JP | 60-123761 A1 | 7/1985 |
| JP | 6-63444 A * | 3/1994 |

OTHER PUBLICATIONS

U.S. Appl. No. 12/701,774, filed Feb. 8, 2010, Egami et al.
U.S. Appl. No. 12/715,617, filed Mar. 2, 2010, Tokuda et al.
U.S. Appl. No. 12/715,644, filed Mar. 2, 2010, Tokuda et al.
U.S. Appl. No. 12/715,661, filed Mar. 2, 2010, Tokuda et al.

* cited by examiner

*Primary Examiner* — Richard L Chiesa
(74) *Attorney, Agent, or Firm* — Burr & Brown

(57) ABSTRACT

A particulate matter detection device (100) includes a first electrode (10) that includes a conductive section (12) and a dielectric (14) that covers the conductive section (12), and a second electrode (20) that is disposed opposite to the first electrode (10) at an interval of 0.3 to 3.0 mm. Charged particulate matter contained in a fluid that passes through the space between the first electrode (10) and the second electrode (20), or particulate matter that is contained in a fluid and charged by a discharge that occurs due to application of a voltage between the electrodes (10) and (20) is electrically adsorbed on at least one of the electrodes (10) and (20), and the particulate matter adsorbed on the electrodes (10) and (20) is detected by measuring a change in electrical properties of the first electrode (10), or a change in electrical properties of the electrodes (10) and (20).

18 Claims, 6 Drawing Sheets

PARTICULATE MATTER DETECTION DEVICE

BACKGROUND OF THE INVENTION

The present invention relates to a particulate matter detection device. More particularly, the present invention relates to a particulate matter detection device that has a reduced size, shows only a small measurement error, and can be produced inexpensively.

A flue exhaust gas or a diesel engine exhaust gas contains particulate matter (PM) such as soot or the like and has been a cause for air pollution. A filter (diesel particulate filter: DPF) made of a ceramic or the like has been widely used to remove a particulate matter. The ceramic DPF can be used for a long period of time, but may suffer defects such as cracks or erosion due to thermal deterioration or the like, so that a small amount of particulate matter may leak from the DPF. It is very important to immediately detect such occurrence of the defects and to recognize the abnormality of a device from the viewpoint of preventing air pollution.

Such defects may be detected by providing a particulate matter detection device on the downstream side of the DPF (e.g., JP-A-60-123761).

SUMMARY OF THE INVENTION

According to JP-A-60-123761, the particulate matter is charged by causing a corona discharge, and an ion current due to the charged particulate matter is measured to determine the amount of the particulate matter. According to this method, since the ion current due to the charged particulate matter is weak, there has been a problem that a large-scale detection circuit is required for detecting such a weak ion current so that cost increases. Moreover, since the particulate matter cannot be effectively charged when the exhaust gas flow rate is large, the amount of particulate matter measured may be smaller than the amount of particulate matter actually contained in the exhaust gas. Therefore, there has also been a problem that a large error occurs.

The present invention was conceived in view of the above problems. An object of the present invention is to provide a particulate matter detection device that has a reduced size, shows only a small measurement error, and can be produced inexpensively.

To achieve the above object, according to the present invention, there is provided a particulate matter detection device as follows.

[1] A particulate matter detection device comprising: a first electrode that extends in one direction and includes a conductive section and a dielectric that covers the conductive section, and a second electrode that extends in one direction and is formed of a metal or an alloy, the first electrode and the second electrode being disposed opposite to each other at an interval of 0.3 to 3.0 mm, the particulate matter detection device being configured so that charged particulate matter contained in a fluid that passes through the space between the first electrode and the second electrode, or particulate matter contained in a fluid that passes through the space between the first electrode and the second electrode and is charged by a discharge that occurs due to application of a voltage between the first electrode and the second electrode can be electrically adsorbed on at least one of the first electrode and the second electrode, and the particulate matter adsorbed on the first electrode and the second electrode can be detected by measuring a change in electrical properties of the first electrode, or a change in electrical properties of the first electrode and the second electrode.

[2] The particulate matter detection device according to [1], wherein the dielectric that forms the first electrode is at least one compound selected from the group consisting of alumina, cordierite, mullite, glass, zirconia, magnesia, silicon, and titania.

[3] The particulate matter detection device according to [1] or [2], wherein the metal or the alloy that forms the second electrode contains at least one element selected from the group consisting of iron, nickel, platinum, copper, gold, molybdenum, and tungsten.

[4] The particulate matter detection device according to any one of [1] to [3], further comprising a heating section that is disposed in the first electrode.

[5] The particulate matter detection device according to any one of [1] to [4], further comprising a takeout lead terminal connected to the first electrode, the takeout lead terminal being disposed between one end and the other end of the first electrode.

[6] The particulate matter detection device according to any one of [1] to [5], the particulate matter detection device being configured so that particulate matter adsorbed on a surface of at least one of the first electrode and the second electrode can be oxidized and removed by causing a discharge to occur between the first electrode and the second electrode by applying a voltage between the first electrode and the second electrode.

[7] The particulate matter detection device according to any one of [1] to [6], wherein the discharge that occurs between the first electrode and the second electrode is selected from the group consisting of a silent discharge, a streamer discharge, and a corona discharge.

The particulate matter detection device according to the present invention is configured so that particulate matter contained in exhaust gas that passes through the space between the electrode (i.e., first electrode) that has the conductive section and the dielectric that covers the conductive section and the electrode (i.e., second electrode) that is formed of a metal or an alloy and disposed opposite to the first electrode can be charged by a discharge that occurs by applying a voltage between the electrodes, and electrically adsorbed on at least one (e.g., first electrode) of the electrodes. This makes it possible to measure the mass of particulate matter contained in exhaust gas that flows on the downstream side of a DPF and has passed through the space between the electrodes. Specifically, the particulate matter detection device according to the present invention does not measure the total amount of particulate matter contained in exhaust gas that flows on the downstream side of the DPF, but measures particulate matter that has passed through the space between the electrodes. The amount of particulate matter contained in the entire exhaust gas can be roughly estimated from the measured value. This makes it possible to measure a small amount of particulate matter that has not able to be detected by a conventional inspection method.

Since the particulate matter detection device according to the present invention does not measure the total amount of particulate matter contained in exhaust gas, the size of the particulate matter detection device can be reduced. Therefore, the particulate matter detection device can be installed in a narrow space. Moreover, since the electrodes have a relatively simple configuration, the particulate matter detection device can be produced inexpensively, and exhibits excellent thermal shock resistance and mechanical strength. For example, when one of the electrodes has deteriorated or broken, only one of the electrode that has deteriorated or broken can be replaced. This facilitates repair and maintenance. Moreover, particulate matter can be measured while arbitrarily adjusting the interval between the electrodes depending on the condition of the measurement target exhaust gas.

Since the particulate matter detection device according to the present invention measures only part of exhaust gas (i.e., particulate matter contained in exhaust gas), particulate matter can be effectively charged even if the total flow rate of exhaust gas that flows on the downstream side of the DPF is high, so that a measured value with only a small error can be obtained.

Since the electrodes of the particulate matter detection device are formed to extend in one direction, only the measurement area such as the tip portion of each electrode can be inserted into a pipe through which high-temperature exhaust gas flows while allowing the other end of each electrode to be positioned outside the pipe. Therefore, an area such as a takeout lead terminal of each electrode for which exposure to high temperature is not desirable can be positioned outside the pipe, so that an accurate and stable measurement can be implemented.

DESCRIPTION OF EXEMPLARY EMBODIMENTS

Embodiments of the present invention are described in detail below. Note that the present invention is not limited to the following embodiments. Various modifications and improvements of the design may be appropriately made without departing from the scope of the present invention based on the knowledge of a person having ordinary skill in the art.

[1] Particulate Matter Detection Device

Figure 1:
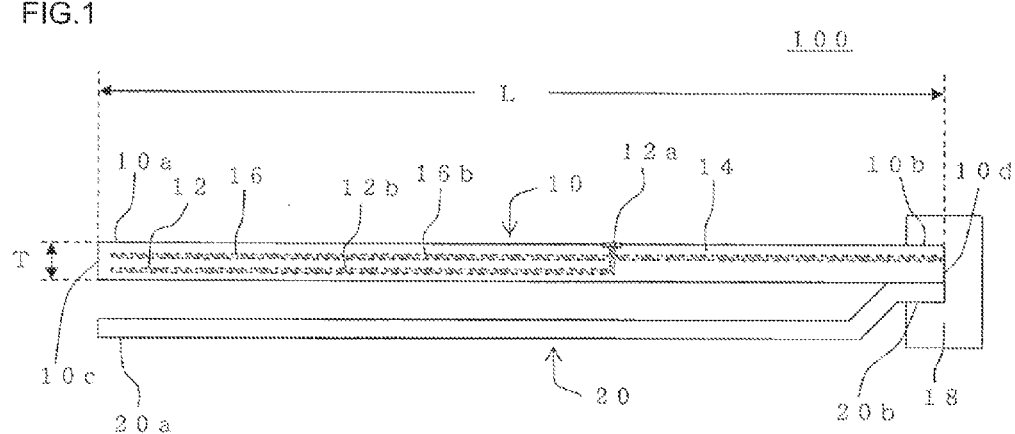
FIG. 1 is a side view schematically showing a particulate matter detection device according to one embodiment of the present invention.
Figure 2:
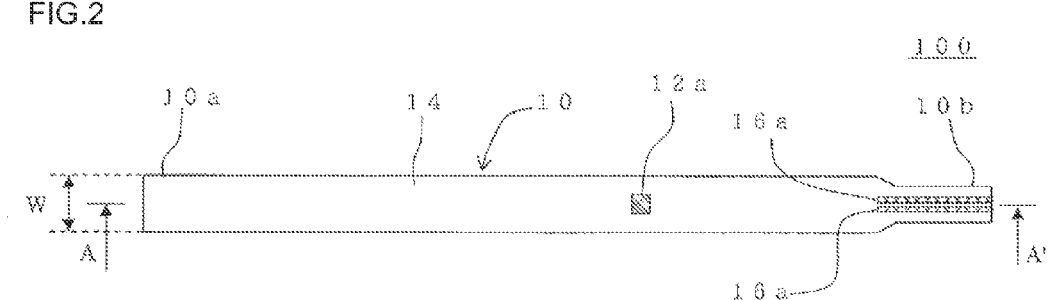
FIG. 2 is a plan view schematically showing a first electrode of a particulate matter detection device according to one embodiment of the present invention.
Figure 3:
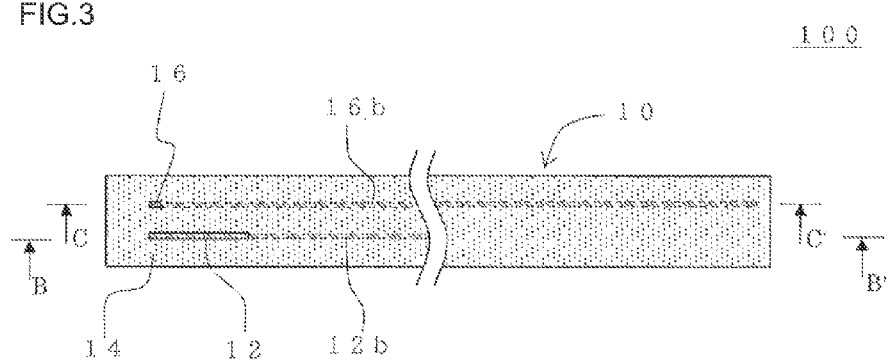
FIG. 3 is a schematic view showing a cross section cut along A-A' line shown in FIG. 2.

FIG. 1 is a side view schematically showing a particulate matter detection device according to one embodiment of the present invention, and FIG. 2 is plan view schematically showing a first electrode of the particulate matter detection device according to one embodiment of the present invention. FIG. 3 is a schematic view showing a cross section cut along A-A' line shown in FIG. 2.

As shown in FIGS. 1 to 3, a particulate matter detection device 100 according to this embodiment includes a first electrode 10 that extends in one direction and includes a conductive section 12 and a dielectric 14 that covers the conductive section 12, and a second electrode 20 that extends in one direction and is formed of a metal or an alloy, the first electrode 10 and the second electrode 20 being disposed opposite to each other at an interval of 0.3 to 3.0 mm.

The particulate matter detection device 100 according to this embodiment is disposed on the downstream side of a filter such as DPF or the like disposed in an exhaust gas passage. The particulate matter detection device 100 is disposed so that the part or entirety of the first electrode 10 and the second electrode 20 (hereinafter may be referred to as "electrodes 10 and 20") are positioned in the exhaust gas passage on the downstream side of the filter to measure particulate matter contained in exhaust gas that passes through the exhaust system.

The particulate matter detection device 100 is configured so that one (i.e., first electrode 10) of the first electrode 10 and the second electrode 20 that are disposed opposite to each other at a given interval is a plate-shaped electrode that extends in one direction and includes the conductive section 12 and the dielectric 14 that covers the conductive section 12, and the other electrode, specifically, second electrode 20 is a plate-shaped electrode that extends in one direction and is formed of a metal or an alloy, as described above. Therefore, when inserting the tip portions of the first electrode 10 and the second electrode 20 into an exhaust gas passage and applying a voltage between the first electrode 10 and the second electrode 20, charged particulate matter contained in a fluid (i.e., exhaust gas) that passes through the space between the first electrode 10 and the second electrode 20, or particulate matter contained in a fluid that passes through the space between the first electrode 10 and the second electrode 20 and is charged by a discharge that occurs due to application of the voltage between the first electrode 10 and the second electrode 20 can be electrically adsorbed on at least one of the first electrode 10 and the second electrode 20. The particulate matter adsorbed on the first electrode 10 and the second electrode 20 can be detected by measuring a change in electrical properties of the first electrode 10 or a change in electrical properties of the first electrode 10 and the second electrode 20. This makes it possible to measure a small amount of particulate matter that cannot be detected by a conventional inspection method.

The amount (i.e., mass) of particulate matter contained in exhaust gas that flows on the downstream side of a DPF and has passed through the space between the electrodes 10 and 20 can be measured using the particulate matter detection device 100 according to this embodiment, and the amount of particulate matter contained in the entire exhaust gas can be roughly estimated from the amount of particulate matter contained in the exhaust gas that has passed through the space between the electrodes 10 and 20.

For example, the relationship between the amount of particulate matter under various flow rate conditions and at least a change in electrical properties of the first electrode is determined in advance by experiments or the like using the particulate matter detection device according to this embodiment, and the amount of particulate matter contained in exhaust gas is calculated from a change in electrical properties (i.e., actual measured value) under the measurement flow rate conditions using the experimental results. Specifically, for example, as for the relation between the amount of particulate matter and the change in electrical property, a change in capacitance of the electrode with respect to the adsorption amount of particulate matter is calculated in advance by experiments. A calibration curve is drawn based on the experimental results, and the amount of particulate matter contained in exhaust gas is calculated using the calibration curve.

Since the particulate matter detection device 100 according to this embodiment does not measure the total amount of particulate matter contained in exhaust gas, the size of the particulate matter detection device can be reduced. Therefore, the particulate matter detection device 100 can be installed in a narrow space such as an automotive exhaust system. Moreover, since, with such a reduction, the electrodes 10 and 20 have a relatively simple configuration (e.g., small and thin), the particulate matter detection device 100 can be produced inexpensively, and exhibits excellent thermal shock resistance and mechanical strength. In addition, for example, when one of the electrodes 10 and 20 has deteriorated or broken, only the electrode that has deteriorated or broken can be replaced. This facilitates repair and maintenance. Moreover, particulate matter can be measured while arbitrarily adjusting the interval between the electrodes depending on the condition of the measurement target exhaust gas.

Since the particulate matter detection device 100 according to this embodiment measures only part of exhaust gas (i.e., particulate matter contained in exhaust gas), particulate matter can be effectively charged even if the total flow of exhaust gas that flows on the downstream side of the DPF is high, so that a measured value with only a small error can be obtained.

Since the electrodes 10 and 20 are formed to extend in one direction, only the measurement area of each electrode such as the tip portions of the electrodes 10 and 20 can be inserted into a pipe through which high-temperature exhaust gas flows while allowing the other end of each electrode to be positioned outside the pipe. Therefore, an area such as takeout lead terminals of the electrodes 10 and 20 for which exposure to high temperature is not desirable can be positioned outside the pipe, so that an accurate and stable measurement can be implemented.

The particulate matter detection device according to this embodiment is particularly effective when particulate matter that passes through the space between the first electrode and the second electrode is soot discharged from a diesel engine.

[1-1] First Electrode

The first electrode is one of a pair of electrodes that serve as the particulate matter detection section. The first electrode extends in one direction, and includes the conductive section and the dielectric that covers the conductive section. Specifically, the first electrode is an electrode in which the conductive section is disposed (buried) in the dielectric. A discharge occurs when applying a voltage between the first electrode and the second electrode that is disposed opposite to the first electrode so that particulate matter contained in exhaust gas is charged and electrically adsorbed on at least one of the first electrode and the second electrode.

The shape and the size of the first electrode are not particularly limited insofar as the first electrode extends in one direction and is plate-like electrode. The shape and the size of the first electrode may be appropriately determined depending on the flow rate of the measurement target exhaust gas, the inner diameter of a pipe to which exhaust gas is discharged, and the like, preferably have a length that allows a particulate matter contained in exhaust gas to be efficiently sampled when inserted into an exhaust gas pipe. For example, when installing the particulate matter detection device in a pipe of an automotive engine (e.g., diesel engine), the first electrode preferably has a longitudinal length of 60 to 130 mm, a thickness of 0.7 to 2.5 mm, and a width of 1.0 to 4.0 mm. The longitudinal length of the first electrode is preferably larger than the thickness of the first electrode by a factor of 20 to 150, and larger than the width of the first electrode by a factor of 15 to 130.

Note that the "longitudinal length of the first electrode" refers to the distance L from one end face 10c to the other end face 10d of the first electrode 10 as shown in FIG. 1, and the "thickness of the first electrode" refers to the distance T from the surface of the first electrode opposite to the second electrode 20 to the surface of the side of the first electrode. The "width of the first electrode" refers to the distance W from one side edge to the other side edge of the first electrode 10 as shown in FIG. 2. Note that the thickness of the first electrode refers to the maximum thickness of the first electrode in the thickness direction, above discussed. When the width of the first electrode is not constant in the longitudinal direction, the width of the first electrode refers to the maximum width of the first electrode in an area in which the conductive section is buried. In FIG. 2, the other end 10b of the first electrode 10 has a reduced width. Note that the other end 10b of the first electrode 10 may or may not have a reduced width.

As shown in FIGS. 1 and 2, the first electrode may be in the shape of a plate having a rectangular cross-sectional shape perpendicular to the longitudinal direction, or may have another shape such as a semicircle insofar as the first electrode extends in one direction.

In the particulate matter detection device according to this embodiment, it is preferable that the first electrode be formed by stacking a plurality of tape-shaped ceramic (which may be referred to as ceramic sheets or green sheets). In this case, since the first electrode can be formed by stacking a plurality of tape-shaped ceramic tapes while interposing the conductive section, a line, and the like between the tape-shaped ceramic, the particulate matter detection device according to this embodiment can be efficiently produced.

[1-1a] Conductive Section

Figure 4:
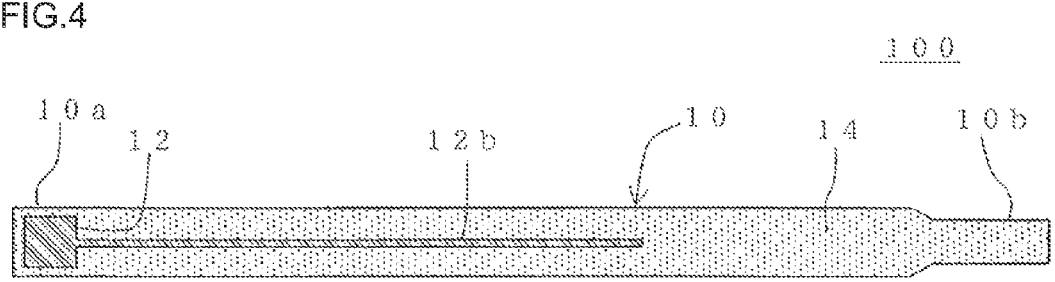
FIG. 4 is a schematic view showing a cross section cut along B-B' line shown in FIG. 3.

The conductive section serves as a substantial electrode area of the first electrode, that is, an area to which a voltage is actually applied. The conductive section is buried in the dielectric. The conductive section is not particularly limited insofar as a discharge occurs between the first electrode and the second electrode and the electrical properties of the first electrode or, more specifically, of the dielectric that forms the first electrode can be detected. For example, the conductive section may be a conductive section 12 shown in FIG. 4 that is disposed at one end of the first electrode 10 and has a rectangular shape or the like. FIG. 4 is a schematic view showing a cross section cut along B-B' line shown in FIG. 3. Note that a plurality of conductive sections may be disposed, and a discharge and electrical property detection may be separately performed using different conductive sections.

For example, when measuring particulate matter using the ends 10a and 20a of the electrodes 10 and 20 of the particulate matter detection device 100 according to this embodiment, the ends 10a and 20a of the electrodes 10 and 20 can be inserted into a pipe through which high-temperature exhaust gas flows while allowing the ends 10b and 20b of the electrodes 10 and 20 to be positioned outside the pipe. Therefore, a takeout lead terminal 12a of the first electrode 10 can be positioned outside the pipe and prevented from being exposed to a high temperature, for example, so that particulate matter can be detected accurately and stably. If the takeout lead terminal 12a is exposed to a high temperature, the particulate matter detection accuracy may decrease. Thus, it may be difficult to stably detect particulate matter, or a contact failure between an electrical terminal and a harness used for external connection may occur during long-term use, and consequently that the particulate matter may not be measured.

Figure 5:
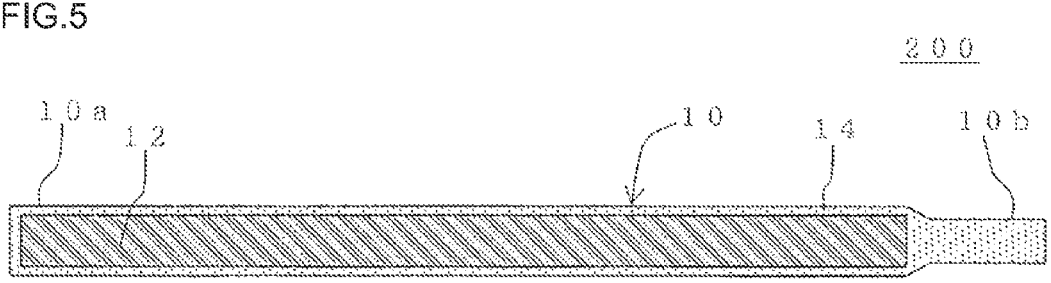
FIG. 5 is a schematic view showing the cross section of a particulate matter detection device according to another embodiment of the present invention.

Note that the conductive section of the first electrode may not be disposed only at one end 10a as shown in FIG. 4. Like a particulate matter detection device 200 shown in FIG. 5 for example, the conductive section 12 can be disposed over a relatively large area (e.g., the entire first electrode) from one end 10a to the other end 10b of the first electrode 10, and covered with the dielectric 14. FIG. 5 is a schematic view showing the particulate matter detection device according to another embodiment of the present invention. The cross section of the first electrode shown in FIG. 5 corresponds to the cross section of the first electrode shown in FIG. 4. The shape of the conductive section is not particularly limited. For example, the conductive section may have a rectangular shape, a circular shape, an elliptical shape, or the like.

This configuration increases the particulate matter adsorption range so that the particulate matter detection capability can be improved. When the conductive section 12 is disposed at one end 10a of the first electrode 10 as shown in FIG. 4, the capacitance between a line 12b connected to the takeout lead terminal 12a and the second electrode 20 (see FIG. 1) may serve as a measurement error. In contrast, such a measurement error can be eliminated by disposing the conductive section 12 over a relatively large area as shown in FIG. 5.

The thickness of the conductive section is not particularly limited insofar as a discharge occurs between the pair of electrodes. The thickness of the conductive section is preferably 5 to 70 μm, for example. Examples of the material for the conductive section include platinum (Pt), molybdenum (Mo), tungsten (W), and the like.

[1-1b] Dielectric

The dielectric that forms the first electrode causes a discharge such as silent discharge, streamer discharge, or corona discharge or the like to occur between the first electrode and the second electrode when applying a voltage between the conductive section of the first electrode and the second electrode. In the first electrode of the particulate matter detection device according to this embodiment, the conductive section is buried in the first electrode, and the dielectric that is disposed to cover the conductive section forms the outer surface of the first electrode.

The dielectric is preferably formed of at least one compound selected from the group consisting of alumina, cordierite, mullite, glass, zirconia, magnesia, silicon, and titania, for example. Among these, alumina is more preferable. The first electrode exhibits excellent heat resistance, dielectric breakdown resistance, and the like when the dielectric is formed of such a material. The term "dielectric" used herein refers to a substance in which dielectricity is predominant over conductivity and behaves as an insulator for a direct-current voltage.

The thickness of the dielectric is not particularly limited. However, for example, the thickness of the dielectric in an area that covers the conductive section on the side opposite to the second electrode is preferably 20 to 300 μm. This allows a discharge to advantageously occur between the first electrode and the second electrode.

[1-1c] Line

When the conductive section is buried in part of the first electrode such as one end thereof, the particulate matter detection device according to this embodiment may include a line 12b that extends from the conductive section 12 of the first electrode 10 to the other end 10b of the first electrode 10 as the particulate matter detection device 100 shown in FIGS. 1 and 4. This configuration makes it possible to apply a voltage to the conductive section 12 through the line 12b. Specifically, the takeout lead terminal 12a of the conductive section 12 can be provided in an area situated at a distance from the conductive section 12. FIGS. 1 and 2 show an example in which the tip portion (i.e., the end that is not connected to the conductive section 12) of the line 12b of the conductive section 12 is via-connected to the takeout lead terminal 12a.

The width of the line 12b is not particularly limited, but is preferably about 0.2 to 1 mm, for example. The thickness of the line 12b is not particularly limited, but is preferably about 5 to 70 μm, for example. Examples of the material for the line 12b include platinum (Pt), molybdenum (Mo), tungsten (W), and the like.

[1-1d] Takeout Lead Terminal

The particulate matter detection device according to this embodiment includes the takeout lead terminal connected to the conductive section that is buried in the dielectric. The takeout lead terminal is electrically connected to the conductive section of the first electrode, and is connected to a line from a power supply or the like used to externally apply a voltage to the conductive section.

In the particulate matter detection device 100 according to this embodiment shown in FIGS. 1 and 2, the takeout lead terminal 12a of the first electrode 10 is disposed between one end 10a and the other end 10b of the first electrode 10.

Therefore, the takeout lead terminal 12a of the first electrode 10 and the electrical connection section (i.e., the other end 20b) of the second electrode 20 that is formed of a metal can be disposed at an interval. This effectively prevents a situation in which a creeping discharge occurs on the surface of the first electrode 10 when applying a voltage to the takeout lead terminal 12a in order to apply a voltage between the pair of electrodes 10 and 20.

Note that the term "one end of the first electrode" used herein refers to an area of the first electrode that corresponds to 30% of the total length of the first electrode 10 from one end face 10c of the first electrode 10. The term "the other end of the first electrode" used herein refers to an area of the first electrode that corresponds to 30% of the total length of the first electrode 10 from the other end face 10*d* of the first electrode 10. Therefore, the area between one end 10*a* and the other end 10*b* of the first electrode 10 refers to the area of the first electrode 10 other than one end 10*a* and the other end 10*b*.

In the particulate matter detection device 100 according to this embodiment, the distance between the other end 20*b* of the second electrode 20 and the takeout lead terminal 12*a* of the conductive section 12 of the first electrode 10 is preferably 5 to 100 mm, and more preferably 10 to 70 mm. If the distance between the other end 20*b* of the second electrode 20 and the takeout lead terminal 12*a* is less than 5 mm, a short circuit due to a creeping discharge may easily occur. If the distance between the other end 20*b* of the second electrode 20 and the takeout lead terminal 12*a* is more than 100 mm, when installing the particulate matter detection device 100 in a pipe or the like so that the other end 20*b* of the second electrode 20 is positioned outside the pipe, the electrodes 10 and 20 may protrude from the pipe to a large extent. This makes it difficult to install the particulate matter detection device 100 in a narrow space.

The shape and the size of the takeout lead terminal 12*a* are not particularly limited. For example, the takeout lead terminal 12*a* preferably has a polygonal such as quadrangular shape having a width of 0.5 to 3 mm and a length of 0.5 to 3 mm. Note that the takeout lead terminal 12*a* may have a circular shape, an elliptical shape, a racetrack shape, or the like. Examples of the material for the takeout lead terminal 12*a* include nickel (Ni), platinum (Pt), chromium (Cr), tungsten (W), molybdenum (Mo), aluminum (Al), gold (Au), silver (Ag), copper (Cu), stainless steel, kovar, and the like.

[1-1e] Heating Section

Figure 6:
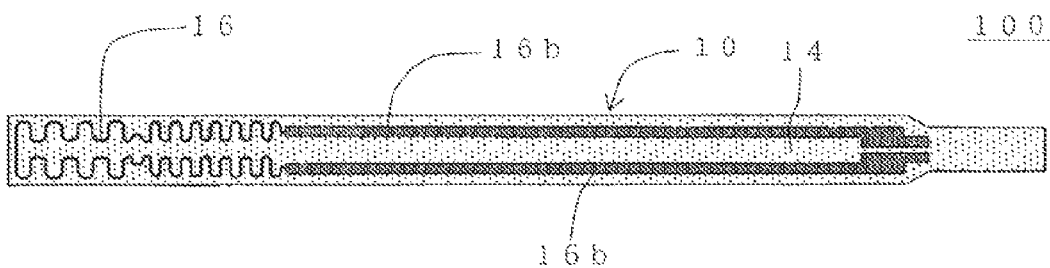
FIG. 6 is a schematic view showing a cross section cut along C-C' line shown in FIG. 3.

As shown in FIGS. 1, 3, and 6, the particulate matter detection device 100 according to this embodiment preferably further includes a heating section 16 that is disposed in the first electrode 10. Particulate matter adsorbed on the first electrode 10 can be oxidized by heating the first electrode 10 using the heating section 16, as described above. Moreover, the temperature of the space between the first electrode 10 and the second electrode 20 can be adjusted to a desired temperature when measuring the mass of the particulate matter so that a change in electrical properties of the electrodes 10 and 20 can be stably measured. FIG. 6 is a schematic view showing a cross section C-C' shown in FIG. 3.

The heating section 16 may be in the shape of a wide film. As shown in FIG. 6, it is preferable that the heating section 16 be formed by disposing a linear metal material in a wave-like manner and turning the metal material in the shape of the letter U at the tip portion. This makes it possible to uniformly heat the first electrode 10. Note that an arbitrary number of heating sections 16 may be disposed in an arbitrary arrangement in order to appropriately adjust the temperature, and oxidize and remove the collected particulate matter.

Examples of the material for the heating section 16 include platinum (Pt), molybdenum (Mo), tungsten (W), and the like. It is preferable that the heating section 16 be disposed near the area of the first electrode 10 where the conductive section 12 is disposed so that at least the area where the conductive section 12 is disposed can be heated, in addition to the area where the conductive section 12 is disposed. For example, the heating section 16 may be formed over the entire first electrode 10. Thus, for example, the heating section can be formed to extend to the other end 10*b* of the first electrode 10. This makes it possible to reduce the difference in temperature between each area of the first electrode 10 so that the first electrode 10 rarely breaks even if the first electrode 10 is rapidly heated. The heating section 16 preferably increases the temperature of the space between the electrodes 10 and 20 to 650° C. or more.

The heating section 16 is preferably disposed at a position opposite to the second electrode 20 with respect to the conductive section 12 of the first electrode 10 interposed therebetween. This configuration prevents a situation in which the heating section 16 hinders a discharge that occurs due to the conductive section 12 of the first electrode 10 and the second electrode 20 so that a discharge advantageously occurs between the electrodes 10 and 20. Moreover, a change in electrical properties of the electrodes 10 and 20 can be easily measured without being affected by the heating section 16.

As shown in FIG. 2, a takeout lead terminal 16*a* (see FIG. 2) of the heating section 16 is also preferably disposed at the other end 10*b* of the first electrode 10. In the particulate matter detection device 100 according to this embodiment as shown in FIG. 6, the heating section 16 is connected to lines 16*b* and 16*b* that are via-connected to the takeout lead terminals 16*a* and 16*a* shown in FIG. 2. The effects of heat when one end 10*a* of the first electrode 10 is heated can be prevented by disposing the takeout lead terminal 16*a* of the heating section 16 at the other end 10*b* of the first electrode 10. In FIG. 2, the takeout lead terminals 16*a* and 16*a* of the heating section 16 are disposed in two rows side by side at the other end 10*b* of the first electrode 10. Note that the arrangement of the takeout lead terminals 16*a* is not limited thereto.

As shown in FIG. 6, when the heating section 16 is linear (see FIG. 6), the width of the heating section 16 is not particularly limited, but is preferably about 0.05 to 1 mm, for example. The thickness of the heating section 16 is not particularly limited, but is preferably about 5 to 30 µm, for example. The width of the line 16*b* is not particularly limited, but is preferably about 0.7 to 4 mm, for example. The thickness of the line 16*b* is not particularly limited, but is preferably about 5 to 30 µm, for example. The width of the takeout lead terminal 16*a* connected to the heating section 16 is not particularly limited, but is preferably about 0.1 to 2 mm, for example. The thickness of the takeout lead terminal 16*a* is not particularly limited, but is preferably about 5 to 1000 µm, for example. Examples of the material for the line 16*b* and the takeout lead terminal 16*a* include nickel (Ni), platinum (Pt), chromium (Cr), tungsten (W), molybdenum (Mo), aluminum (Al), gold (Au), silver (Ag), copper (Cu), stainless steel, kovar, and the like.

The particulate matter detection device 100 according to this embodiment preferably further includes a heating power supply that is connected to the takeout lead terminal 16*a* of the heating section 16. The heating power supply may be a constant current power supply or the like.

Note that the particulate matter detection device according to this embodiment may not include the heating section, and oxidize and remove particulate matter adsorbed on the surface of the electrode by causing a discharge to occur by applying a voltage between the electrodes. When oxidizing and removing particulate matter by causing a discharge to occur, the field intensity is preferably 5 to 200 kV/cm, and the amount of energy supplied is 0.05 to 10 J/µg with respect to the treatment target substance.

[1-2] Second Electrode

The second electrode is the other of the pair of electrodes that serve as the particulate matter detection section. The second electrode extends in one direction, and is formed of a metal or an alloy and disposed opposite to the first electrode at a given interval.

The particulate matter detection device according to this embodiment detects given electrical properties between the pair of electrodes to measure a change in electrical properties of the first electrode or a change in electrical properties of the first electrode and the second electrode to detect particulate matter adsorbed on the first electrode and the second electrode. The second electrode may be utilized as a ground electrode when detecting given electrical properties of the first electrode and the second electrode, for example. The ground electrode refers to an electrode that is grounded.

Figure 7:
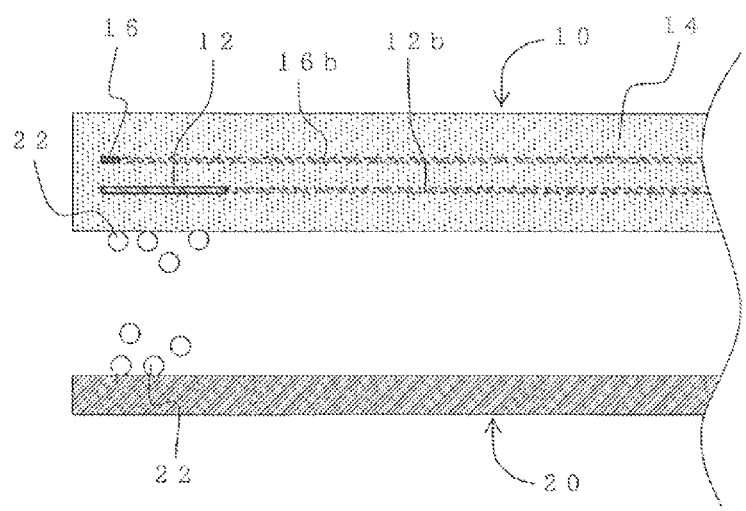
FIG. 7 is a cross-sectional view showing a particulate matter measurement method using a particulate matter detection device according to one embodiment of the present invention.

As shown in FIG. 7, the particulate matter detection device 100 according to this embodiment causes a discharge to occur by applying a voltage of 20 to 200 kV/cm between the first electrode 10 and the second electrode 20 at a power of 0.1 to 10 W though the voltage and the power vary depending on the distance (gap) between the electrodes and the exhaust gas temperature, so that particulate matter 22 contained in exhaust gas is electrostatically collected on the electrodes 10 and 20, and calculates the mass of the adsorbed particulate matter from a change in impedance calculated from the capacitances or the like before and after collection to detect the particulate matter (mass) contained in the exhaust gas, for example. A change in capacitance may be measured by generating an applied signal having a measurement voltage 1 to 10 of V (AC) and a frequency of 1 to 100 kHz, for example.

FIG. 7 is a cross-sectional view showing a particulate matter measurement method using the particulate matter detection device according to one embodiment of the present invention. In FIG. 7, the elements configured in the same manner as the elements of the particulate matter detection device shown in FIGS. 1 to 3 are indicated by the same symbols. Description of these elements is omitted.

The second electrode may be a plate-shaped member that is formed of a metal or an alloy and allows a discharge to occur between the first electrode and the second electrode. The second electrode may be formed of a material that contains at least one element selected from the group consisting of iron, nickel, platinum, copper, gold, molybdenum, and tungsten. Examples of the alloy include stainless steel, kovar, and the like. It is preferable to use stainless steel that exhibits excellent corrosion resistance and thermal conductivity and is inexpensive.

The second electrode preferably has a size (surface area) almost equal to that of the first electrode that is disposed opposite to the second electrode. The thickness of the second electrode is not particularly limited, but is preferably 0.5 to 2.0 mm, for example.

Since the second electrode is formed of a metal or an alloy, particulate matter adsorbed on the second electrode can be heated and oxidized by applying a voltage to the second electrode to generate heat, for example. The second electrode may be electrically separately connected to an electrode regeneration/purification heating power supply.

In the particulate matter detection device according to this embodiment, the distance between the first electrode and the second electrode is 0.3 to 3.0 mm, and preferably 0.5 to 1.5 mm. This ensures that a discharge effectively occurs between the electrodes.

[1-3] Other Elements

As shown in FIG. 1, the particulate matter detection device according to this embodiment may further include a connector section 18 that holds the electrodes 10 and 20 parallel to each other at a given interval, and electrically connects the electrodes 10 and 20 and each power supply, for example.

The connector section 18 is preferably formed of a ceramic material having insulation properties such as alumina. The connector section 18 is preferably shaped so that the connector section 18 can sufficiently hold the dielectric by sandwiching each side of the end of the dielectric. It is also preferable that the connector section 18 can be assembled with the line due to contact with each takeout lead terminal of the dielectric at the same time the dielectric is sandwiched.

The particulate matter detection device 100 according to this embodiment preferably further includes a discharge power supply that is connected to the takeout lead terminal 12a or the like. The discharge power supply is preferably a high-voltage alternating-current power supply or direct-current power supply, for example. A pulse voltage, an alternating-current voltage (e.g., rectangular wave), or the like is preferably applied when causing a discharge to occur. The applied voltage is preferably 50 to 200 kV/cm, although the applied voltage may vary depending on the distance (gap) between the electrodes and the exhaust gas temperature. The power supplied when applying a voltage is preferably 0.1 to 10 W.

When particulate matter contained in a fluid (i.e., exhaust gas) that passes through the space between the electrodes 10 and 20 is not charged, the particulate matter detection device 100 according to this embodiment causes a discharge to occur between the electrodes 10 and 20 so that the particulate matter is charged and electrically adsorbed on the surface of each electrode as discussed before. When particulate matter contained in a fluid that passes through the space between the electrodes 10 and 20 has already been charged, for example, the particulate matter need not necessarily be charged by causing a discharge to occur. Specifically, the charged particulate matter can be electrically adsorbed on the surface of the electrodes 10 and 20 without causing a discharge to occur between the electrodes 10 and 20.

As discussed above, when charging particulate matter by causing a discharge to occur between the electrodes, the charged particulate matter is electrically drawn to the electrode that has a polarity opposite to that of the charged particulate matter during a discharge, and adsorbed on the surface of the electrode. On the other hand, when particulate matter has already been charged before the particulate matter passes through the space between the electrodes, the charged particulate matter is electrically drawn to the electrode that has a polarity opposite to that of the charged particulate matter by applying a given voltage between the electrodes. The voltage applied between the electrodes when particulate matter has already been charged is preferably 4 to 40 kV/cm.

As discussed above, since the particulate matter detection device 100 according to this embodiment calculates the mass of the adsorbed particulate matter from a change in impedance calculated from the capacitance or the like before and after collection, the particulate matter detection device 100 according to this embodiment preferably further includes a measurement section (not shown) that measures the impedance between the electrodes 10 and 20. Examples of the measurement section include an LCR meter, an impedance analyzer, and the like that can measure impedance in addition to capacitance.

Figure 8:
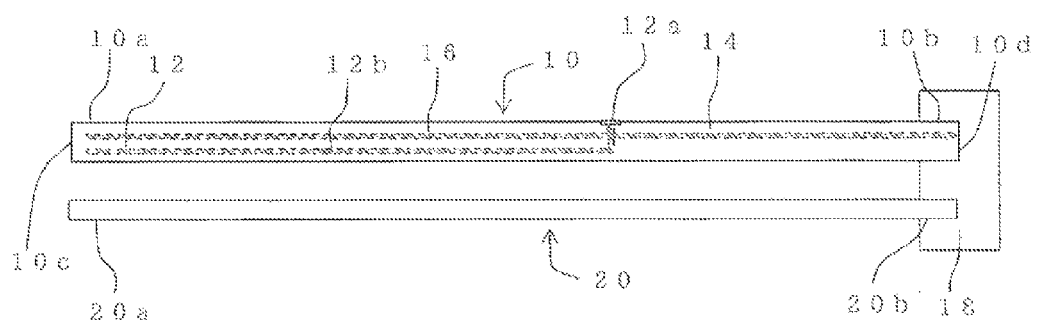
FIG. 8 is a side view schematically showing a particulate matter detection device according to another embodiment of the present invention.

In FIG. 1, the second electrode 20 is bent toward the side of the first electrode 10 at the other end 20b so that the other end 10b of the first electrode 10 comes in contact with the other end 20b of the second electrode 20, and the other end 10b of the first electrode 10 and the other end 20b of the second electrode 20 are held by the connector section 18. As shown in FIG. 8, the first electrode 10 and the second electrode 20 may be parallel plate-type electrodes that are disposed parallel at a given interval from one ends 10a and 20a to the other ends 10b and 20b, and the other ends 10b and 20b may be held by the connector section 18, for example. FIG. 8 is a side view schematically showing a particulate matter detection device according to another embodiment of the present invention. In FIG. 8, the elements configured in the same manner as the elements of the particulate matter detection device shown in FIG. 1 are indicated by the same symbols. Thus, description of these elements is omitted.

[1-4] Method of Installing Exhaust System

As shown in FIGS. 9A to 9D, a particulate matter detection device 400 according to the present invention may be disposed so that the first electrode 10 and the second electrode 20 are disposed at a given interval by bonding (holding) the second electrode 20 to an outer cylinder 30 of the cylindrical particulate matter detection device, and holding the first electrode 10 using an insulating holding member 19 so that the first electrode 10 is electrically insulated from (does not come in contact with) the outer cylinder 30, for example.

Figure 9A:
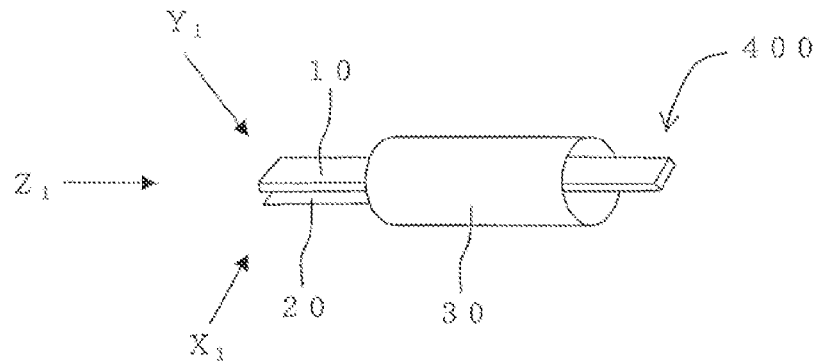
FIG. 9A is a perspective view schematically showing a particulate matter detection device according to still another embodiment of the present invention.
Figure 9B:
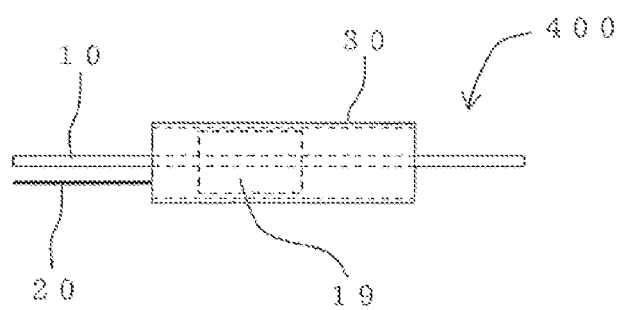
FIG. 9B is a side view showing the particulate matter detection device shown in FIG. 9A viewed from the direction $X_1$.
Figure 9C:
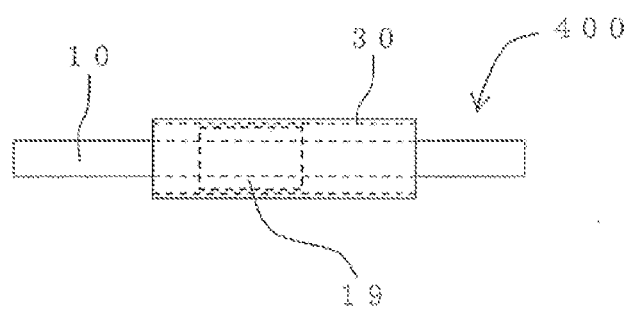
FIG. 9C is a side view showing the particulate matter detection device shown in FIG. 9A viewed from the direction $Y_1$.
Figure 9D:
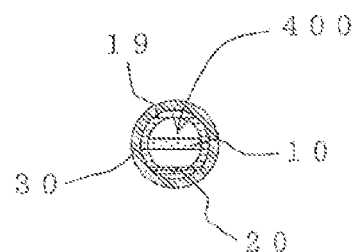
FIG. 9D is a front view showing the particulate matter detection device shown in FIG. 9A viewed from the direction $Z_1$.

FIG. 9A is a perspective view schematically showing a particulate matter detection device according to still another embodiment of the present invention, FIG. 9B is a side view showing the particulate matter detection device shown in FIG. 9A viewed from the direction $X_1$, FIG. 9C is a side view showing the particulate matter detection device shown in FIG. 9A viewed from the direction $Y_1$, and FIG. 9D is a front view showing the particulate matter detection device shown in FIG. 9A viewed from the direction $Z_1$.

In the particulate matter detection device 400 shown in FIGS. 9A to 9D, the second electrode 20 may be bonded to the outer cylinder 30 by welding, for example. The holding member 19 may be an insulating member that is in the shape of a tubular body that has an outer diameter corresponding to the inner diameter of the outer cylinder 30 (i.e., a tubular body that has an outer diameter that allows the tubular body to be fitted into the outer cylinder 30), and can hold the first electrode 10 therein. The holding member 19 may be formed of an insulating ceramic material such as alumina.

Figure 10:
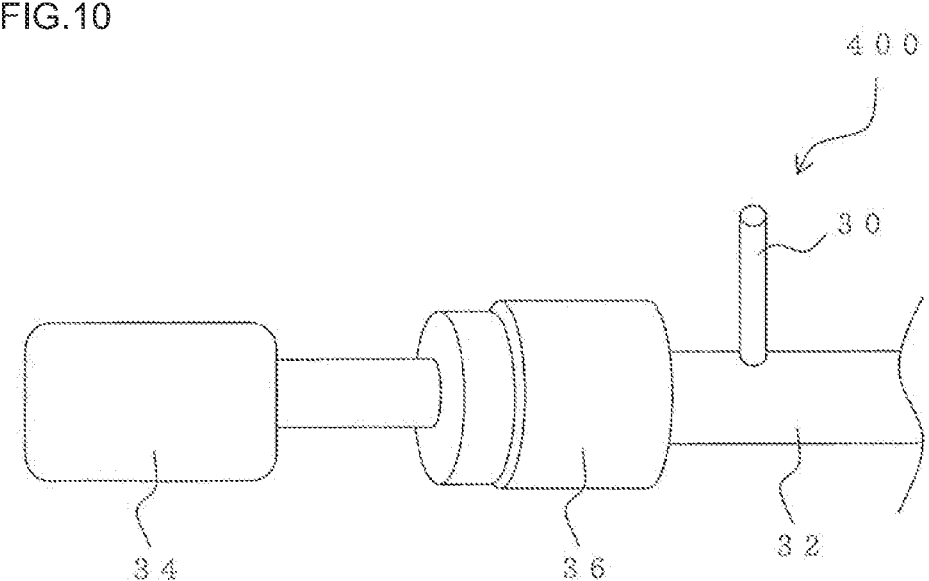
FIG. 10 is a perspective view showing a state in which a particulate matter detection device according to the present invention is installed in a pipe through which exhaust gas flows.

As shown in FIG. 10, a threaded hole having a diameter almost equal to that of the outer cylinder 30 of the particulate matter detection device 400 is formed in a pipe 32 through which flue exhaust gas or diesel engine exhaust gas flows, and the first electrode 10 and the second electrode 20 held by the outer cylinder 30 (see FIG. 9A) are inserted into the threaded hole from one end, for example. When inserting the first electrode 10 and the second electrode 20 (see FIG. 9A) into the pipe 32, the pipe 32 and the outer cylinder 30 may be threadably secured so that the center position of the conductive section 12 of the first electrode (see FIGS. 4 and 5) coincides with the center position of the pipe 32 through which exhaust gas flows (i.e., the center position in a cross section perpendicular to the circulation direction), for example. In FIG. 10, reference numeral 34 indicates an engine, and reference numeral 36 indicates a filter such as a diesel particulate filter (DPF).

In the particulate matter detection device according to the present invention shown in FIG. 9A, the second electrode 20 is bonded to the outer cylinder 30. Meanwhile, in a particulate matter detection device 500 shown in FIGS. 11A to 11D, the first electrode 10 and the second electrode 20 can be held by an insulating tubular holding member 19 in a state in which the first electrode 10 and the second electrode 20 are disposed at a given interval, and the holding member 19 is fitted into the outer cylinder 30, for example.

Figure 11A:
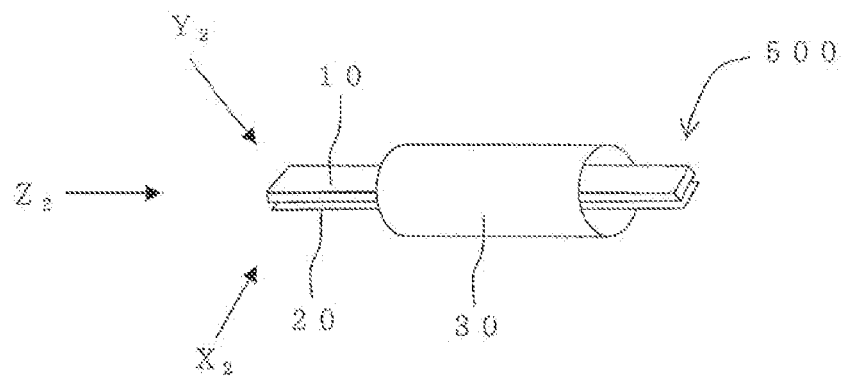
FIG. 11A is a perspective view schematically showing a particulate matter detection device according to still another embodiment of the present invention.
Figure 11B:
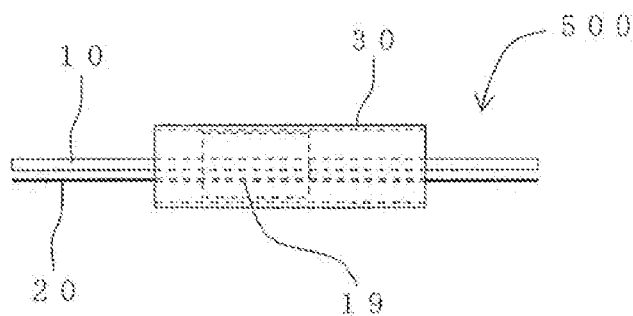
FIG. 11B is a side view showing the particulate matter detection device shown in FIG. 11A viewed from the direction $X_2$.
Figure 11C:
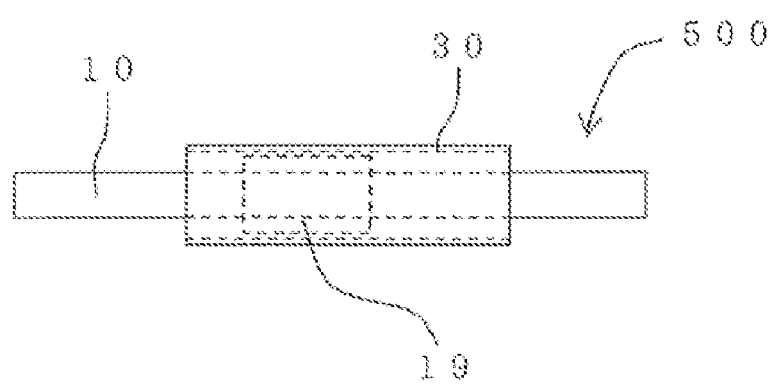
FIG. 11C is a side view showing the particulate matter detection device shown in FIG. 11A viewed from the direction $Y_2$.
Figure 11D:
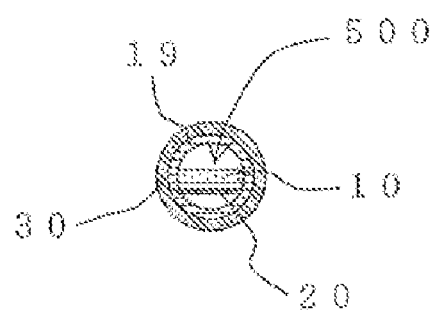
FIG. 11D is a front view showing the particulate matter detection device shown in FIG. 11A viewed from the direction $Z_2$.

FIG. 11A is a perspective view schematically showing a particulate matter detection device according to still another embodiment of the present invention, FIG. 11B is a side view showing the particulate matter detection device shown in FIG. 11A viewed from the direction $X_2$, FIG. 11C is a side view showing the particulate matter detection device shown in FIG. 11A viewed from the direction $Y_2$, and FIG. 11D is a front view showing the particulate matter detection device shown in FIG. 11A viewed from the direction $Z_2$.

In the particulate matter detection device 500 shown in FIGS. 11A to 11D, the first electrode 10 and the second electrode 20 are held by the holding member 19 in a state in which the first electrode 10 and the second electrode 20 do not come in contact with the outer cylinder 30 (i.e., are electrically insulated from the outer cylinder 30).

Note that the particulate matter detection device according to this embodiment may be installed in an exhaust system (pipe) by another method. Specifically, the amount of particulate matter contained in exhaust gas that has passed through the space between the electrodes can be detected to calculate the amount of particulate matter contained in the entire exhaust gas can be calculated if at least part of the first electrode and the second electrode that are disposed opposite to each other is installed in a passage (pipe) through which exhaust gas flows, and at least part of the exhaust gas passes through the space between the electrodes.

[2] Method of Producing Particulate Matter Detection Device

A method of producing the particulate matter detection device according to this embodiment is described below.

The particulate matter detection device according to this embodiment is produced as follows. Specifically, a dielectric raw material that forms a dielectric and other components used as a forming raw material are mixed to each other to prepare a slurried forming raw material. A green sheet is produced using the slurried forming raw material. A conductive section is formed on the surface of the green sheet using a conductive material optionally together with a line to obtain a conductive section green sheet. Another green sheet is stacked on the conductive section green sheet to obtain a green sheet laminate. The green sheet laminate is then fired to obtain a first electrode in which the conductive section is disposed (buried) in the dielectric.

When disposing a heating section in the first electrode, a heating section is formed on the surface of further another green sheet using a conductive material optionally together with a line, a takeout lead terminal, and the like connected to the heating section to obtain a heating section green sheet. The above conductive section green sheet, the heating section green sheet, and another green sheet are stacked to obtain a green sheet laminate. With the above constitution, the obtained green sheet laminate is then fired. A first electrode in which the conductive section and the heating section are buried therein is thus produced.

The first electrode thus obtained and a second electrode formed of a metal or an alloy are disposed opposite to each other at a given interval to obtain a particulate matter detection device according to this embodiment. An example of producing the first electrode 10 of the particulate matter detection device 100 according to this embodiment shown in FIG. 1 is described in detail below.

[2-1] Preparation of Forming Raw Material

At least one ceramic raw material (dielectric raw material) selected from the group consisting of alumina, a cordierite-forming raw material, mullite, glass, zirconia, magnesia, silicon, and titania and other components used as a forming raw material are mixed to each other to prepare a slurried forming raw material. The above raw material is preferable as the ceramic raw material (dielectric raw material). Note that the ceramic raw material is not limited thereto. As the components other than the ceramic raw material, it is preferable to use a binder, a plasticizer, a dispersant, a dispersion medium, and the like.

The binder is not particularly limited. An aqueous binder or a non-aqueous binder may be used. For example, as the aqueous binder, methyl cellulose, polyvinyl alcohol, polyethylene oxide, or the like may be suitably used. As the non-aqueous binder, polyvinyl butyral, an acrylic resin, polyethylene, polypropylene, or the like may be suitably used. Preferable examples of the acrylic resin include a (meth)acrylic resin, a (meth)acrylate copolymer, an acrylate-methacrylate copolymer, and the like.

The binder is preferably added in an amount of 3 to 20 parts by mass, and more preferably 6 to 17 parts by mass, with respect to 100 parts by mass of the dielectric raw material. If the amount of the binder is within the above range, cracks or the like do not occur when forming the slurried forming raw material into a green sheet, or when drying and firing the green sheet.

As the plasticizer, glycerine, polyethylene glycol, dibutyl phthalate, di(2-ethylhexyl) phthalate, diisononyl phthalate, or the like may be used.

The plasticizer is preferably added in an amount of 30 to 70 parts by mass, and more preferably 45 to 55 parts by mass, with respect to 100 parts by mass of the binder. If the amount of the plasticizer is more than 70 parts by mass, the resulting green sheet becomes too soft and may be deformed when processing the green sheet. If the amount of the plasticizer is less than 30 parts by mass, the resulting green sheet becomes too hard so that cracks may occur when merely bending the green sheet, resulting in the deterioration in the handling capability.

As the dispersant, an aqueous dispersant such as anionic surfactant, wax emulsion, or pyridine, or a non-aqueous dispersant such as fatty acid, phosphate, or synthetic surfactant may be used.

The dispersant is preferably added in an amount of 0.5 to 3 parts by mass, and more preferably 1 to 2 parts by mass, with respect to 100 parts by mass of the dielectric raw material. If the amount of the dispersant is less than 0.5 parts by mass, the dispersibility of the dielectric raw material may decrease. As a result, cracks or the are occurred in the green sheet. If the amount of the dispersant is more than 3 parts by mass, the amount of impurities may increase during firing although the dispersibility of the dielectric raw material remains the same.

As the dispersion medium, water or the like may be used. The dispersion medium is preferably added in an amount of 50 to 200 parts by mass, and more preferably 75 to 150 parts by mass, with respect to 100 parts by mass of the dielectric raw material.

The above materials are sufficiently mixed using an alumina pot and alumina cobblestone to prepare a slurried forming raw material for forming a green sheet. The slurried forming raw material may be prepared by mixing the materials by ball milling using a mono ball.

Next the obtained slurried forming raw material for forming a green sheet is stirred under reduced pressure to remove bubbles, and the viscosity of the slurried forming raw material is adjusted to a given value. The viscosity of the slurried forming raw material thus prepared is preferably 2.0 to 6.0 Pa·s, more preferably 3.0 to 5.0 Pa·s, and particularly preferably 3.5 to 4.5 Pa·s. The slurry can be easily formed into a sheet by adjusting the viscosity of the slurry to a value within the above range. It may be difficult to form the slurry into a sheet if the viscosity of the slurry is too high or too low. The viscosity of the slurry refers to a value measured using a Brookfield viscometer.

[2-2] Forming Process

The slurried forming raw material obtained by the above method is formed into a tape to obtain a green sheet that extends in one direction. The forming process method is not particularly limited insofar as a green sheet can be formed by forming the forming raw material into a sheet. The conventionally known methods such as a doctor blade method, a press forming method, a rolling method, a calender roll method, or the like may be used. The thickness of the green sheet is preferably 50 to 800 µm.

[2-3] Formation of Green Sheet Laminate

A conductive section, a line, a heating section, and a takeout lead terminal are formed on the surface of the obtained green sheet. For example, a conductive paste for forming a conductive section, a line, a heating section, and a takeout lead terminal to be disposed is prepared. The thus obtained conductive paste is printed on the green sheet at corresponding positions as shown in FIGS. 4 and 6 to form a conductive section, a line, a heating section, and a takeout lead terminal.

The above conductive paste may be prepared by adding a binder and a solvent such as terpineol to a powder that contains at least one component selected from the group consisting of gold, silver, platinum, nickel, molybdenum, and tungsten depending on the materials necessary for forming the conductive section, line, etc., and sufficiently kneading the mixture using a triple roll mill or the like. The conductive paste may be printed by an arbitrary method. For example, screen printing or the like may be used.

More specifically, a conductive section is formed at one end of one side of one green sheet, and a line that extends from the conductive section to the other end is formed to obtain a conductive section green sheet. A heating section is formed on another green sheet at a position at which the heating section overlaps at least the conductive section when stacked on the conductive section green sheet. A line that extends from the heating section to the other end is formed to obtain a heating section green sheet.

A plurality of the green sheets thus obtained is stacked according to the configuration of the first electrode to obtain a green sheet laminate.

[2-4] Firing

The obtained green sheet laminate is dried and fired to obtain a first electrode. Specifically, the resulting green sheet laminate is dried at 60 to 150° C., and fired at 1200 to 1600° C. to obtain a first electrode. When the green sheet contains an organic binder, the green sheet is preferably debinded at 400 to 800° C. before firing.

According to the above production method, the first electrode can be efficiently produced. Note that the method of producing the particulate matter detection device according to this embodiment is not limited to the above method. The second electrode may be conveniently produced by cutting a conductive metal plate corresponding to the shape of the second electrode, for example.

EXAMPLES

The present invention is further described below by way of examples. Note that the present invention is not limited to the following examples.

Example 1

Preparation of Forming Raw Material

An alumina pot was charged with alumina as dielectric raw material, polyvinyl butyral as binder, di(2-ethylhexyl) phthalate as plasticizer, sorbitan trioleate as dispersant, and an organic solvent (xylene:butanol=6:4 (mass ratio)) as dispersion medium. The components were mixed to prepare a slurried forming raw material for forming a green sheet. 7 parts by mass of the binder, 3.5 parts by mass of the plasticizer, 1.5 parts by mass of the dispersant, and 100 parts by mass of the organic solvent were used with respect to 100 parts by mass of alumina.

The slurried forming raw material thus obtained was stirred under reduced pressure to remove bubbles, and the viscosity of the slurried forming raw material was adjusted to 4 Pa·s. The viscosity of the slurry was measured using a Brookfield viscometer.

(Forming Process)

The slurried forming raw material obtained by the above method was formed into a sheet using a doctor blade method. The thickness of the green sheet was 250 µm. Each green sheet was punched to have a given external shape.

A conductive section, a heating section, a line, and a takeout lead terminal as shown in FIGS. 1, 2, 4, and 6 were formed on the surface of the green sheet. A conductive paste for forming the conductive section, heating section, line, and takeout takeout lead terminal was prepared by adding 2-ethylhexanol as solvent, polyvinyl butyral as binder, di(2-ethylhexyl) phthalate as plasticizer, sorbitan trioleate as dispersant, alumina as green sheet common material, and a glass frit as sintering aid to a tungsten powder, and sufficiently kneading the mixture using a kneader and a triple roll mill. The above raw materials were used so that tungsten:alumina:glass frit:2-ethylhexanol:polyvinyl butyral:di(2-ethylhexyl) phthalate: sorbitan trioleate=75.5:15:5:50:7:3.5:1 (mass ratio).

The conductive section, the line, the takeout lead terminal, and the heating section having a given shape were formed by screen printing using the paste obtained by the above method.

More specifically, a conductive section was formed at one end of one side of one green sheet, and a line extending from the conductive section to the other end was formed to obtain a conductive section green sheet. A heating section was formed on another green sheet at a position at which the heating section overlaps at least the conductive section when stacked on the conductive section green sheet. A line extending from the heating section to the other end was formed to obtain a heating section green sheet. The conductive section had dimensions of 5×2.5 mm.

The side of the heating section green sheet opposite to the side on which the heating section was formed was stacked on the side of the conductive section green sheet on which the conductive section was formed. Another green sheet (green sheet on which the conductive section and the heating section were not formed) was stacked on the side of the heating section green sheet on which the heating section was formed to obtain a green sheet laminate. The line and the takeout lead terminal were via-connected using a conductive paste. The green sheets were stacked under pressure using a heating-type uniaxial press machine.

(Firing)

The green sheet laminate thus obtained was dried at 120° C., and fired at 1500° C. to form a first electrode. The resulting first electrode was in the shape of a rectangular parallelepiped having a length of 116 mm, a width of 3 mm, and a thickness of 1 mm.

(Production of Second Electrode)

As a second electrode, a stainless steel plate having a length of 116 mm, a width of 3 mm, and a thickness of 1 mm was used. The second electrode had a flat shape in which the other end 20b was not bent as shown in FIG. 8.

(Production of Particulate Matter Detection Device)

The first electrode and the second electrode were disposed parallel to each other at an interval of 0.75 mm, and the takeout lead terminal of each electrode was connected to a connector section to produce a particulate matter detection device. The connector section was formed using alumina to have such a shape that the connector section could hold the dielectric by sandwiching the ends of the first electrode and the second electrode. The connector section had dimensions of 10 mm×8.0 mm×10 mm. The takeout lead terminals of the first electrode and the second electrode and lines connected to the following measuring instrument were electrically connected through the connector section. The second electrode served as a ground electrode.

(Discharge Power Supply)

A pulse power supply and a DC power supply were used as discharge power supplies.

(Measurement Section)

An impedance analyzer manufactured by Agilent Technologies was used as a measurement section that measures the impedance between the electrodes. The measurement section was connected to the takeout lead terminal of the first electrode. The takeout lead terminal of the ground electrode was grounded.

(Particulate Matter Measurement Method)

The particulate matter detection device was installed in the subsequent stage (downstream side) of a filter disposed in a pipe connected to a diesel engine. A direct-injection diesel engine of displacement: 2000 cc was used as the diesel engine. An exhaust gas was discharged at an engine speed of 1500 rpm, a torque of 24 N·m, an exhaust gas recirculation (EGR) rate of 50%, an exhaust gas temperature of 200° C., and an air intake of 1.3 m$^3$/min (room temperature).

When charging and collecting particulate matter, a DC voltage of 2.0 kV (current: 0.1 mA) was applied to the first electrode so that a discharge occurred between the first electrode and the second electrode in order to collect particulate matter at each electrodes by charging. Before charging and collecting particulate matter, the initial capacitance (pF) between the pair of electrodes was measured for one minute six times. After charging and collecting particulate matter for one minute under the above conditions, the charging/collection operation was stopped. Again, the capacitance (pF) (capacitance between the pair of the electrodes after collecting particulate matter for one minute) was measured for one minute six times. The average value of the six measured values was calculated for each of the initial capacitance and the capacitance after collecting particulate matter for one minute. The mass of the collected particulate matter was calculated from the difference between the initial capacitance and the capacitance after collecting particulate matter for one minute. A calibration curve was drawn in advance for a change in capacitance with respect to the adsorption amount of particulate matter, and the mass of the collected particulate matter was calculated using the calibration curve. The capacitance between the electrodes was measured at an applied voltage (AC) of 2 V and a frequency of 10 kHz. The results are shown in Table 1.

TABLE 1

|  | Capacitance |
|---|---|
| Initial | 0.58 pF |
| After collecting particulate matter for one minute | 0.87 pF |

After completion of the above measurements, the particulate matter collected (adsorbed) on the first electrode and the second electrode was oxidized (cleaned) by heating. Specifically, as the cleaning operation, a voltage of 27 V (current: 4 A or more) was applied to the heating section of the first electrode and the second electrode to increase the temperature of each electrode to 700° C. to heat and oxidize the particulate matter. The cleaning operation was performed at intervals of 15 minutes. Thus, each electrode of the particulate matter detection device according to the present invention could be regenerated and purified by the cleaning operation so that an accurate and stable measurement could be successively performed for a long period of time.

The particulate matter detection device according to the present invention may be suitably used to immediately detect the occurrence of defects and to recognize the abnormality of a DPF. This makes it possible to contribute to preventing air pollution.

What is claimed is:

1. A particulate matter detection device comprising:
a first electrode that extends in one direction and includes a conductive section and a dielectric that covers the conductive section; and
a second electrode that extends in one direction and is formed of a metal or an alloy,
wherein the first electrode and the second electrode being disposed opposite to each other at an interval of 0.3 to 3.0 mm,
the particulate matter detection device being configured so that charged particulate matter contained in a fluid that passes through the space between the first electrode and the second electrode, or particulate matter contained in a fluid that passes through the space between the first electrode and the second electrode and is charged by a discharge that occurs due to application of a voltage between the first electrode and the second electrode can be electrically adsorbed on at least one of the first electrode and the second electrode, and the particulate matter adsorbed on the first electrode and the second electrode can be detected by measuring a change in electrical properties of the first electrode, or a change in electrical properties of the first electrode and the second electrode.

2. The particulate matter detection device according to claim 1, wherein the dielectric that forms the first electrode is at least one compound selected from the group consisting of alumina, cordierite, mullite, glass, zirconia, magnesia, silicon, and titania.

3. The particulate matter detection device according to claim 1, wherein the metal or the alloy that forms the second electrode contains at least one element selected from the group consisting of iron, nickel, platinum, copper, gold, molybdenum, and tungsten.

4. The particulate matter detection device according to claim 1, further comprising a heating section that is disposed in the first electrode.

5. The particulate matter detection device according to claim 1, further comprising a takeout lead terminal connected to the first electrode, the takeout lead terminal being disposed between one end and the other end of the first electrode.

6. The particulate matter detection device according to claim 1, the particulate matter detection device being configured so that particulate matter adsorbed on a surface of at least one of the first electrode and the second electrode can be oxidized and removed by causing a discharge to occur between the first electrode and the second electrode by applying a voltage between the first electrode and the second electrode.

7. The particulate matter detection device according to claim 1, wherein the discharge that occurs between the first electrode and the second electrode is selected from the group consisting of a silent discharge, a streamer discharge, and a corona discharge.

8. The particulate matter detection device according to claim 2, wherein the metal or the alloy that forms the second electrode contains at least one element selected from the group consisting of iron, nickel, platinum, copper, gold, molybdenum, and tungsten.

9. The particulate matter detection device according to claim 2, further comprising a heating section that is disposed in the first electrode.

10. The particulate matter detection device according to claim 3, further comprising a heating section that is disposed in the first electrode.

11. The particulate matter detection device according to claim 8, further comprising a heating section that is disposed in the first electrode.

12. The particulate matter detection device according to claim 2, further comprising a takeout lead terminal connected to the first electrode, the takeout lead terminal being disposed between one end and the other end of the first electrode.

13. The particulate matter detection device according to claim 3, further comprising a takeout lead terminal connected to the first electrode, the takeout lead terminal being disposed between one end and the other end of the first electrode.

14. The particulate matter detection device according to claim 8, further comprising a takeout lead terminal connected to the first electrode, the takeout lead terminal being disposed between one end and the other end of the first electrode.

15. The particulate matter detection device according to claim 4, further comprising a takeout lead terminal connected to the first electrode, the takeout lead terminal being disposed between one end and the other end of the first electrode.

16. The particulate matter detection device according to claim 9, further comprising a takeout lead terminal connected to the first electrode, the takeout lead terminal being disposed between one end and the other end of the first electrode.

17. The particulate matter detection device according to claim 10, further comprising a takeout lead terminal connected to the first electrode, the takeout lead terminal being disposed between one end and the other end of the first electrode.

18. The particulate matter detection device according to claim 11, further comprising a takeout lead terminal connected to the first electrode, the takeout lead terminal being disposed between one end and the other end of the first electrode.

* * * * *